(12) United States Patent
Fujii (10) Patent No.: US 7,764,766 B2
(45) Date of Patent: Jul. 27, 2010

(54) X-RAY APPARATUS

(75) Inventor: Hideki Fujii, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/528,651

(22) PCT Filed: Mar. 1, 2007

(86) PCT No.: PCT/JP2007/053896

§ 371 (c)(1),
(2), (4) Date: Aug. 26, 2009

(87) PCT Pub. No.: WO2008/120293

PCT Pub. Date: Sep. 10, 2008

(65) Prior Publication Data

US 2010/0061507 A1    Mar. 11, 2010

(51) Int. Cl.
*H05G 1/56*    (2006.01)
(52) U.S. Cl. .................... 378/114; 378/116
(58) Field of Classification Search .......... 378/62, 378/96, 97, 98.11, 98.12, 108–112, 114–116
See application file for complete search history.

(56) References Cited

FOREIGN PATENT DOCUMENTS

| JP | 2-44699 A | 2/1990 |
|---|---|---|
| JP | 9-298099 A | 11/1997 |
| JP | 2000-173795 A | 6/2000 |
| JP | 2005-253801 A | 9/2005 |
| JP | 2006-116137 A | 5/2006 |

OTHER PUBLICATIONS

International Search Report for the Application No. PCT/JP2007/053896 mailed May 22, 2007.

*Primary Examiner*—Courtney Thomas
(74) *Attorney, Agent, or Firm*—Cheng Law Group, PLLC (57) ABSTRACT

An X-ray apparatus according to this invention includes an X-raying condition fixing controller for carrying out controls to cause an X-ray emission from an X-ray tube on X-raying conditions effective when an X-ray emission is stopped by the automatic exposure controller, and turning off automatic exposure control by the automatic exposure controller. Thus, the automatic exposure control is carried out only at the time of starting radiography, and a subsequent sequential shooting can be carried out in the state of X-raying conditions at that time being locked and the automatic exposure control being turned off. When X-raying a new site to be imaged after a current site to be imaged, driving of a top board is detected during the sequential shooting, and the automatic exposure control can be carried out only at the time of starting radiography for the new site to be imaged, and a subsequent sequential shooting can be carried out in the state of locking to the X-raying conditions effective at that time, with the automatic exposure control turned off. As a result, a proper automatic exposure control can be carried out without setting a radiographic collection mode.

3 Claims, 5 Drawing Sheets

X-RAY APPARATUS

TECHNICAL FIELD

This invention relates to an X-ray apparatus for emitting X rays from an X-ray emitting device to a radiographic subject to acquire X-ray fluoroscopic images of the radiographic subject, and more particularly to a technique for carrying out a proper automatic exposure control without setting a radiographic acquisition mode.

BACKGROUND ART

Conventionally, X-ray radiography with an X-ray apparatus is carried out based on X-raying conditions including a tube voltage, a tube current and an emission time of an X-ray tube. In certain cases, an automatic exposure control is carried out to end (cut off) the emission of X rays from the X-ray tube when X rays emitted from the X-ray tube and transmitted through a subject have reached a predetermined amount, to keep the contrast of X-ray fluoroscopic images in an optimal state. That is, the automatic exposure control aims at keeping film density constant through an automatic control of exposure time. Specifically, the control is intended to obtain a desired film density by converting an amount of X rays transmitted through a subject into electric signals, and cutting off X rays when this amount of electricity reaches a fixed value (see Patent Document 1).

In certain cases, a flat panel X-ray detector (hereinafter abbreviated as "FPD") is provided in place of the film in the X-ray apparatus noted above. The FPD has a sensitive film laminated on a substrate, detects X rays incident on the sensitive film, converts the detected X rays into electric charges, and stores the electric charges in capacitors arranged in a two-dimensional array. The stored electric charges are read by turning on switching elements, and are fed as X-ray detection signals into an image processor disposed at a subsequent stage. Then, the image processor provides X-ray fluoroscopic images based on the X-ray detection signals.

Further, an X-ray apparatus with this FPD may have a sequential shooting function as well as the above-noted automatic exposure control function. That is, the above-noted automatic exposure control is carried out at each shooting time of the sequential shooting. Specifically, when radiography (X-ray emission) is started and an amount of transmitted X rays reaches a predetermined value, the X-ray emission is stopped by the above-noted automatic exposure control to complete the current radiography. The automatic exposure control is carried out for a next radiography also. Thus, a plurality of consecutive X-ray fluoroscopic images are acquired under automatic exposure control operating constantly (at each emission).

Before starting a sequential shooting radiography, the operator (e.g. an X-ray radiographer) needs to set a radiographic collection mode to this X-ray apparatus, such as a subtraction mode, a mode of moving a radiographic system or a fluoroscopic table, or, conversely, a non-moving mode, in order to determine whether to carry out the sequential shooting radiography in a state of locking (fixing) X-raying conditions or in a state of automatic exposure control. The subtraction mode is, for example, for acquiring subtraction images (difference images) based on differences between mask images (images before injection of a contrast medium) and live images (images after injection of the contrast medium). The mode of moving a radiographic system or a fluoroscopic table is, for example, for radiographing a plurality of sites to be imaged of a subject successively by moving the radiographic system or the fluoroscopic table. The non-moving mode is, for example, for radiographing a single site to be imaged of a subject without moving the radiographic system or the fluoroscopic table.

[Patent Document 1]
Unexamined Patent Publication No. 2000-173795 (page 2, FIG. 11)

DISCLOSURE OF THE INVENTION

Problems to be Solved by the Invention

However, the conventional X-ray apparatus have the following problems. In a sequential shooting for acquiring subtraction images, forgetting to set the subtraction mode will result in a problem that X-raying conditions are not locked, but the automatic exposure control is constantly operational to conduct radiography on various X-raying conditions, thereby failing to obtain proper subtraction images (difference images). The same will occur with an X-ray apparatus combined with a digital processing device without a function to notify setting of the above mode. Even if the subtraction mode is set, when a plurality of sites are X-rayed as in leg DSA (digital subtraction angiography), and when the automatic exposure control is carried out once at the time of first radiography for the first site to be imaged, the X-raying conditions at that time will be locked. This results in a problem that proper subtraction images (difference images) cannot be obtained since radiography is conducted on the X-raying conditions as they are even if the radiographic system or the fluoroscopic table is moved to make a shift to other sites to be imaged.

Supposing the above "non-moving mode" is set and the automatic exposure control function is constantly on when live images are acquired through sequential shooting without moving the radiographic system and fluoroscopic table, there arises a problem that, under the influence of a contrast medium such as barium, all the frames in a series of live images cannot obtain a uniform luminance level.

That is, there is a problem that a proper automatic exposure control cannot necessarily be carried out only with setting of the radiographic acquisition mode.

However, if X-raying conditions are locked unconditionally, when a plurality of sites are X-rayed, it will become impossible to turn on the automatic exposure control function for each site to be imaged, resulting in a problem that proper radiographic images cannot be obtained.

This invention has been made having regard to the state of the art noted above, and its object is to provide an X-ray apparatus which can carry out proper automatic exposure control without setting a radiographic acquisition mode.

Means for Solving the Problems

To fulfill the above object, this invention provides the following construction.

An X-ray apparatus according to this invention is an X-ray apparatus for X-raying a subject, comprising (A) a top board for supporting, or contactable by, the subject; (B) an X-ray emitting device for emitting X rays toward the subject on the top board; (C) an X-ray detecting device opposed to the X-ray emitting device across the top board for detecting X rays emitted from the X-ray emitting device and transmitted through the subject; (D) a storage device for storing X-raying conditions indicating conditions of X-ray emission from the X-ray emitting device; (E) a radiography start instruction input device for receiving X-ray radiography start inputs; (F)

a drive instruction input device for receiving instruction inputs for driving at least one of the X-ray emitting device and the X-ray detecting device, and the top board; (G) a drive control device for performing drive control of at least one of the X-ray emitting device and the X-ray detecting device, and the top board, based on an instruction from the drive instruction input device; (H) an input detecting device for detecting a start instruction from the radiography start instruction input device or a drive instruction from the drive instruction input device during a sequential shooting; (I) an automatic exposure control device for starting, based on an input detection by the input detecting device, an X-ray emission from the X-ray emitting device on X-raying conditions read from the storage device, and for stopping the X-ray emission from the X-ray emitting device when an amount of transmitted X rays detected by the X-ray detecting device reaches a predetermined value; and (J) an X-raying condition fixing control device for carrying out controls to cause an X-ray emission from the X-ray emitting device on X-raying conditions effective when the X-ray emission is stopped by the automatic exposure control device, and turning off the automatic exposure control by the automatic exposure control device, until a next input is detected by the input detecting device.

According to the X-ray apparatus of this invention, the X-ray emitting device emits X rays toward the patient on the top board. The X-ray detecting device is opposed to the X-ray emitting device across the top board for detecting X rays emitted from the X-ray emitting device and transmitted through the subject. The storage device stores X-raying conditions indicating conditions of X-ray emission from the X-ray emitting device. The radiography start instruction input device receives X-ray radiography start inputs. The drive instruction input device receives instruction inputs for driving at least one of the X-ray emitting device and the X-ray detecting device, and the top board. The drive control device performs drive control of at least one of the X-ray emitting device and the X-ray detecting device, and the top board, based on an instruction from the drive instruction input device. The input detecting device detects a start instruction from the radiography start instruction input device or a drive instruction from the drive instruction input device during a sequential shooting. The automatic exposure control device starts, based on an input detection by the input detecting device, an X-ray emission from the X-ray emitting device on X-raying conditions read from the storage device, and stops the X-ray emission from the X-ray emitting device when an amount of transmitted X rays detected by the X-ray detecting device reaches a predetermined value. The X-raying condition fixing control device carries out controls to cause an X-ray emission from the X-ray emitting device on X-raying conditions effective when the X-ray emission is stopped by the automatic exposure control device, and turns off the automatic exposure control by the automatic exposure control device, until a next input is detected by the input detecting device.

Thus, the automatic exposure control can be carried out only at the time of starting radiography, and a subsequent sequential shooting can be carried out in the state of X-raying conditions at that time being locked and the automatic exposure control being turned off. Supposing an attempt is made to carry out X-ray radiography of a new site to be imaged in place of a current site to be imaged, since a drive instruction from the drive instruction input device (i.e. an instruction to drive at least one of the X-ray emitting device and the X-ray detecting device, and the top board) is detected during the sequential shooting, the automatic exposure control can be carried out only at the time of starting radiography for the new site to be imaged by this drive instruction, and a subsequent sequential shooting can be carried out in the state of being locked to the X-raying conditions effective at that time, with the automatic exposure control turned off. As a result, a proper automatic exposure control can be carried out without setting a radiographic collection mode such as a subtraction mode, a mode of moving a radiographic system or a fluoroscopic table, or a non-moving mode.

At a time of sequential shooting for acquiring subtraction images, for example, there is no need for setting a subtraction mode, and a subsequent sequential shooting can be carried out in a state of being locked to X-raying conditions acquired from the automatic exposure control used only at the time of staring radiography, and with the automatic exposure control turned off. This allows a mask image and live images to be obtained on the same X-raying conditions, thereby to obtain proper subtraction images (difference images). Also in the case of an X-ray apparatus combined with a digital processing device without a function of notifying setting of the above mode, proper subtraction images (difference images) can be obtained similarly. When X-ray radiography is carried out for a plurality of sites as in DSA (digital subtraction angiography), the automatic exposure control is carried out once at the time of first radiography for the first site to be imaged, the X-raying conditions at that time can be locked, and X-ray radiography can be carried out on the locked X-raying conditions until a change is made in the sites to be imaged. When a shift is made to a different site to be imaged, by moving the radiographic system or the fluoroscopic table, the automatic exposure control is carried out once at the time of first radiography for the different site to be imaged, and the X-raying conditions at that time can be locked for X-ray radiography. Thus, proper subtraction images (difference images) can be obtained also when X-ray radiography is carried out for a plurality of sites.

Also when a sequential shooting is carried out to acquire live images without moving the radiographic system and fluoroscopic table, there is no need for setting the above-noted "non-moving mode" or the like, and a subsequent sequential shooting can be carried out in a state of being locked to X-raying conditions acquired from the automatic exposure control used only at the time of staring radiography, and with the automatic exposure control turned off. This realizes a uniform luminance for all frames of a series of live images, without being influenced by a contrast medium such as barium.

That is, a proper automatic exposure control can be carried out without setting the radiographic acquisition mode.

X-raying conditions are never locked unconditionally. When X-ray radiography is carried out for a plurality of sites, the automatic exposure control function can be turned on only at the time of starting radiography for each site to be imaged, thereby to obtain proper radiographic images.

Preferably, the X-ray emitting device is an X-ray tube; the X-raying conditions include a tube voltage value of the X-ray tube, a tube current value of the X-ray tube and an X-ray emission time value of the X-ray tube; the automatic exposure control device has an actual radiographing time measuring device for measuring an actual radiographing time after starting the X-ray emission from the X-ray emitting device on the X-raying conditions read from the storage device, based on an input detection by the input detecting device, until the amount of transmitted X rays detected by the X-ray detecting device reaches the predetermined value; and the X-raying condition fixing control device, until a next input is detected by the input detecting device, fixes the actual radiographing time measured by the actual radiographing time measuring device as X-ray emission time on the X-raying conditions, and turns off the automatic exposure control by the automatic exposure control device.

With this construction, the automatic exposure control can be carried out only at the time of starting radiography, and a subsequent sequential shooting can be carried out in the state of X-raying conditions at that time (X-ray emission time of the X-ray tube acquired by the automatic exposure control) being locked and the automatic exposure control being turned off. Supposing an attempt is made to carry out X-ray radiography of a new site to be imaged in place of a current site to be imaged, since a drive instruction from the drive instruction input device (i.e. an instruction to drive at least one of the X-ray emitting device and X-ray detecting device, and the top board) is detected during the sequential shooting, the automatic exposure control can be carried out only at the time of starting radiography for the new site to be imaged by this drive instruction, and a subsequent sequential shooting can be carried out in the state of being locked to the X-raying conditions effective at that time (X-ray emission time of the X-ray tube acquired from the automatic exposure control), with the automatic exposure control turned off. As a result, a proper automatic exposure control can be carried out without setting a radiographic collection mode such as a subtraction mode, a mode of moving a radiographic system or a fluoroscopic table, or a non-moving mode.

Preferably, the storage device stores X-raying conditions indicating conditions of X-ray emission from the X-ray emitting device, for each site to be imaged. In this case, since X-raying conditions for various sites to be imaged are stored, various sites to be imaged can be X-rayed conveniently.

EFFECTS OF THE INVENTION

With the X-ray apparatus according to this invention, the automatic exposure control can be carried out only at the time of starting radiography, and a subsequent sequential shooting can be carried out in the state of X-raying conditions at that time being locked and the automatic exposure control being turned off. Supposing an attempt is made to carry out X-ray radiography of a new site to be imaged in place of a current site to be imaged, since a drive instruction from the drive instruction input device (i.e. an instruction to drive at least one of the X-ray emitting device and the X-ray detecting device, and the top board) are detected during the sequential shooting, the automatic exposure control can be carried out only at the time of starting radiography for the new site to be imaged by this drive instruction, and a subsequent sequential shooting can be carried out in the state of being locked to the X-raying conditions effective at that time, with the automatic exposure control turned off. As a result, a proper automatic exposure control can be carried out without setting a radiographic acquisition mode such as a subtraction mode, a mode of moving a radiographic system or a fluoroscopic table, or a non-moving mode.

DESCRIPTION OF REFERENCES

1 . . . top board
2 . . . X-ray tube (X-ray emitting device)
3 . . . FPD
4 . . . radiography controller
5 . . . emission controller
6 . . . input unit
7 . . . display unit
8 . . . hand switch (radiography start instruction input device)
9 . . . top board drive switch (drive instruction input device)
10 . . . top board drive controller (drive control device)
13 . . . automatic exposure detector (X-ray detecting device)
14 . . . storage unit (storage device)
15 . . . input detector (input detecting device)
16 . . . automatic exposure controller (automatic exposure control device)
17 . . . X-raying condition fixing controller (X-raying condition fixing control device)
18 . . . timer (actual exposure time measuring device)

BEST MODE FOR CARRYING OUT THE INVENTION

An automatic exposure control device, based on an input detection by an input detecting device, starts an X-ray emission from an X-ray emitting device on X-raying conditions read from a storage device, and stops the X-ray emission from the X-ray emitting device when an amount of transmitted X rays detected by an X-ray detecting device reaches a predetermined value. An X-raying condition fixing control device, until a next input is detected by the input detecting device, controls the X-ray emission of the X-ray emitting device to be carried out on the X-raying conditions effective when the X-ray emission is stopped by the automatic exposure control device, and turns off the automatic exposure control by the automatic exposure control device. Thus, the automatic exposure control can be carried out only at a time of starting radiography, and a subsequent sequential shooting can be carried out in a state of the X-raying conditions at that time being locked and the automatic exposure control being turned off. As a result, therefore, the object has been fulfilled of providing an X-ray apparatus which can carry out proper automatic exposure control without setting a radiographic acquisition mode such as a subtraction mode, a mode of moving a radiographic system or a fluoroscopic table, or a non-moving mode.

Embodiment 1

Figure 1:
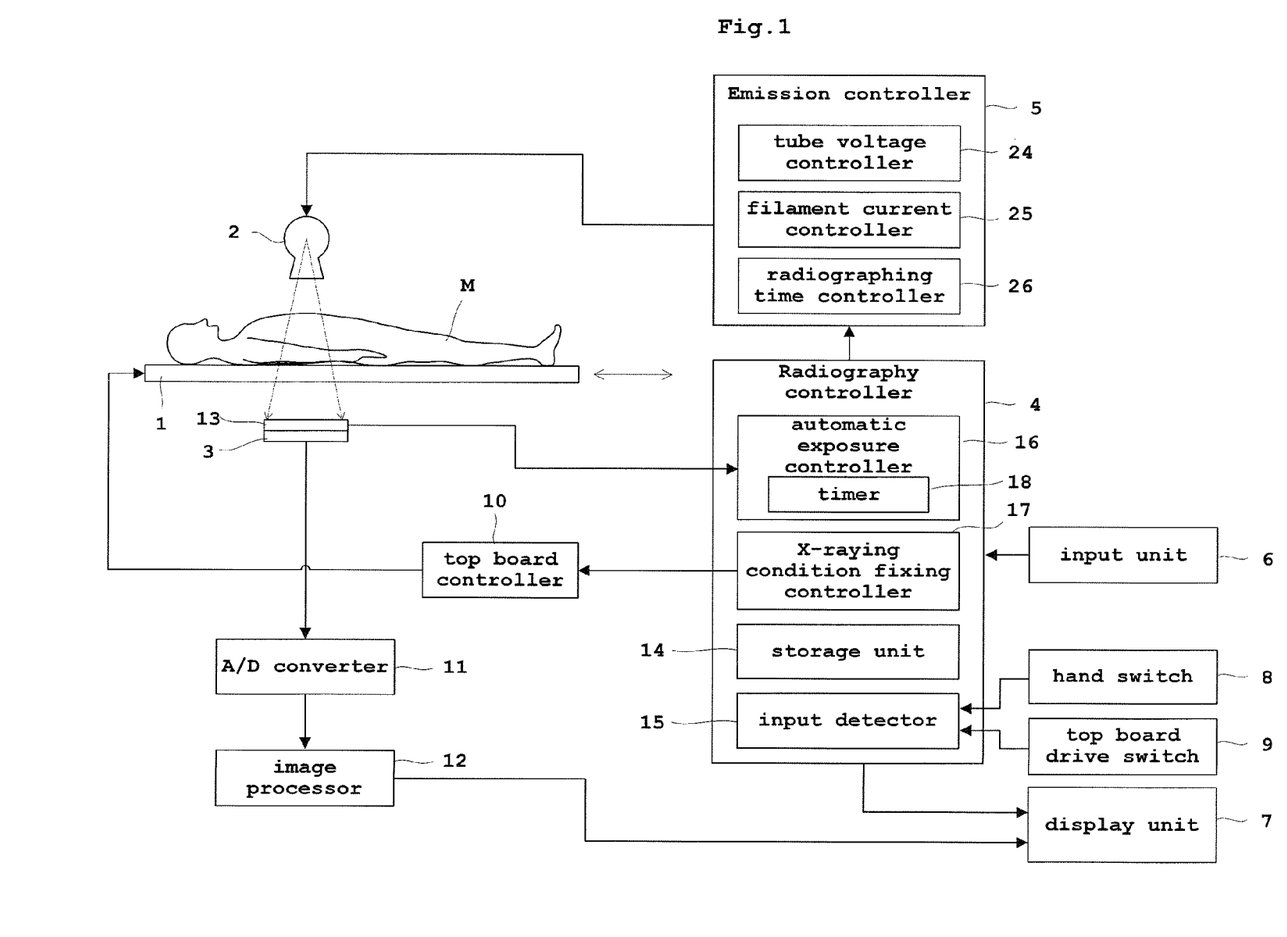
FIG. 1 is a block diagram showing an overall construction of an X-ray apparatus.
Figure 2:
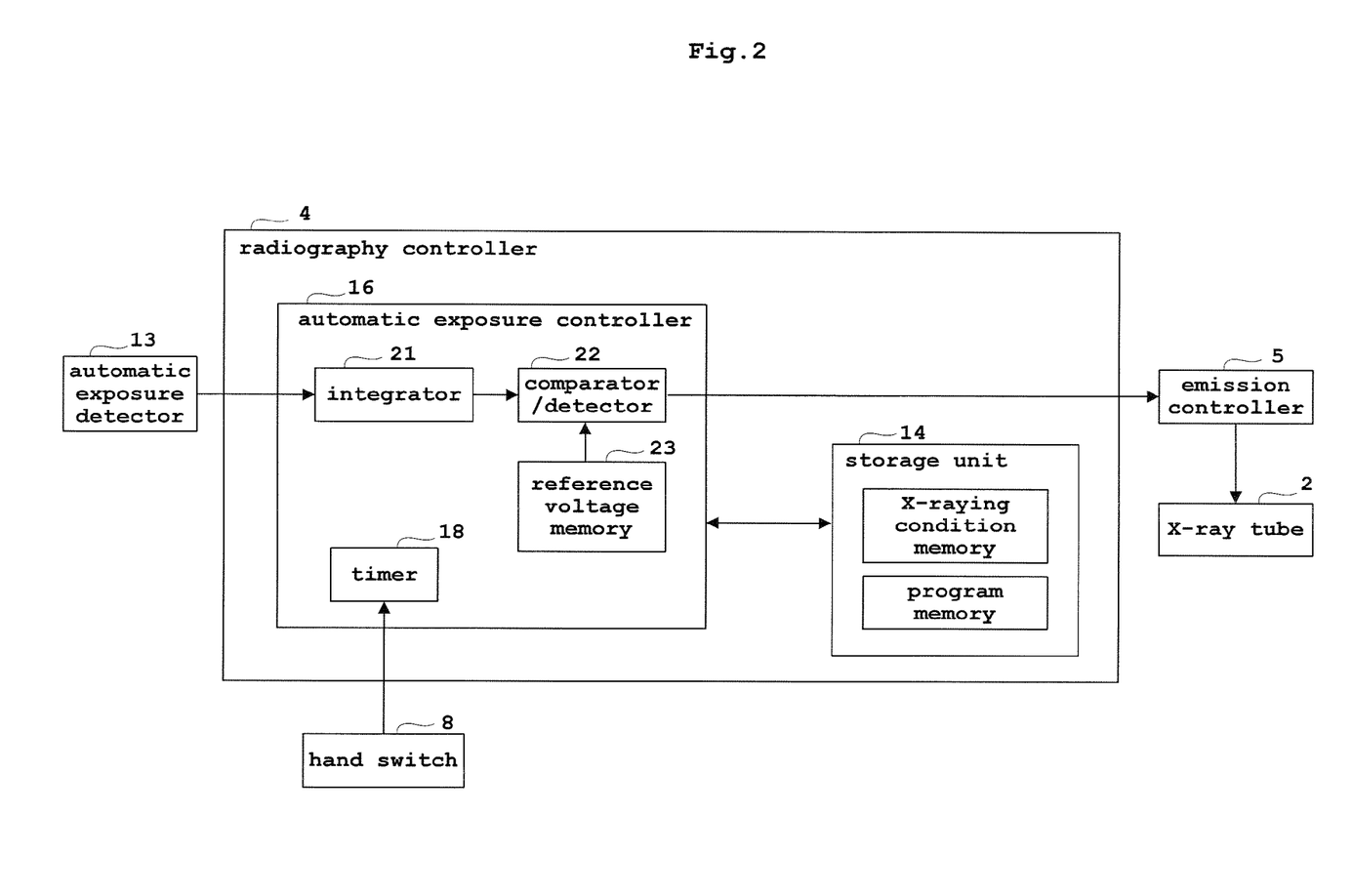
FIG. 2 is a block diagram showing a construction of an automatic exposure controller in Embodiment 1.
Figure 3:
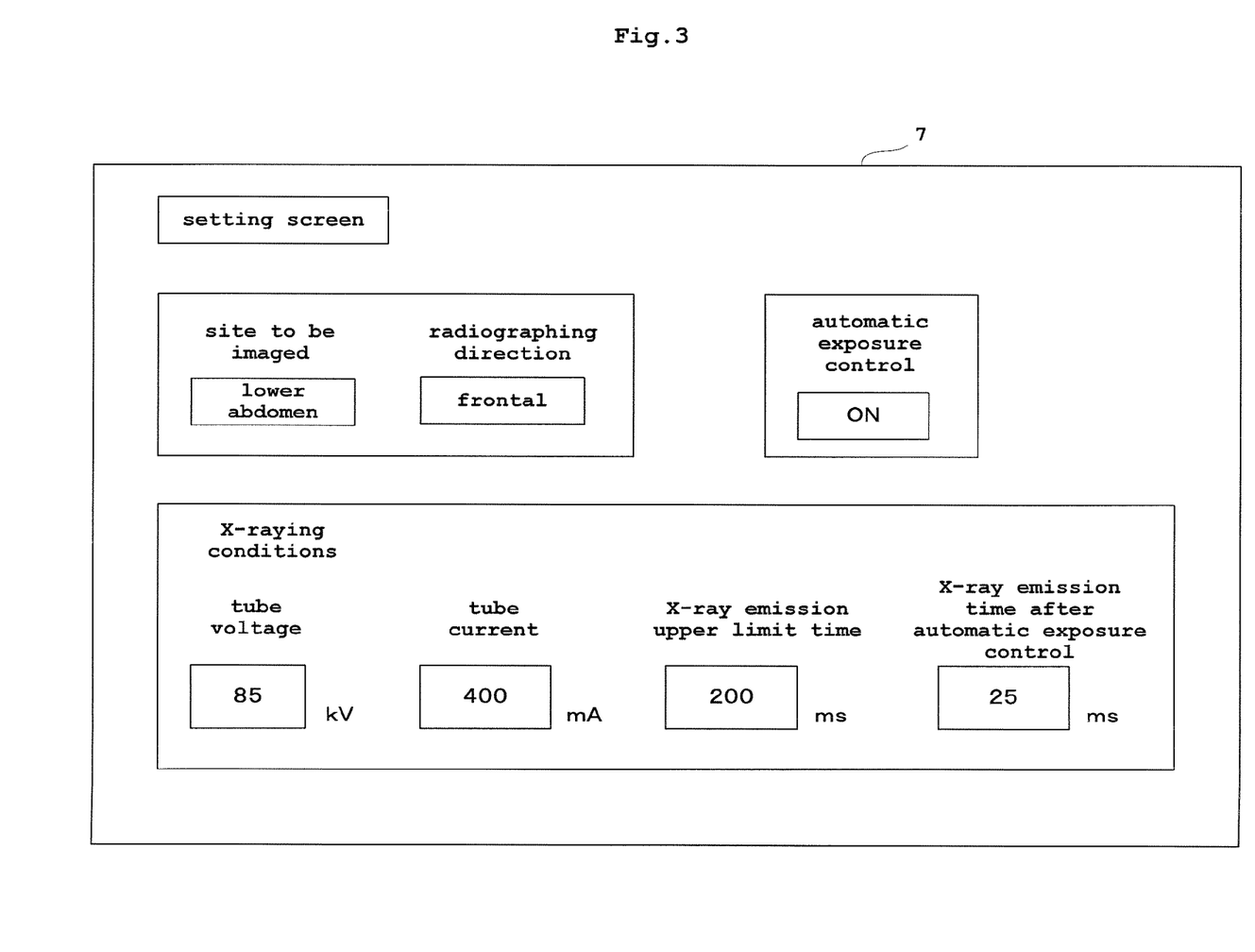
FIG. 3 is a view showing part of a display screen of a display unit.

Embodiment 1 of this invention will be described hereinafter with reference to the drawings. FIG. 1 is a block diagram showing an overall construction of an X-ray apparatus. FIG. 2 is a block diagram showing a construction of an automatic exposure controller in Embodiment 1. FIG. 3 is a view showing part of a display screen of a display unit.

The overall construction of the X-ray apparatus will be described using FIG. 1. As shown in FIG. 1, the X-ray apparatus includes a top board 1 for supporting a subject (patient) M, an X-ray tube 2 for emitting X rays toward the subject M on the top board 1, an FPD 3 opposed to the X-ray tube 2 across the top board 1 for detecting X rays emitted from the X-ray tube 2 and transmitted through the subject M, a radiography controller 4 for performing various controls relating to X-ray radiography, an emission controller 5 for controlling the X-ray tube 2 based on the controls from this radiography controller 4, an input unit 6 for inputting X-raying conditions and the like indicating sites to be imaged and conditions of X-ray emission from the X-ray tube 2, a display unit 7 for displaying the X-raying conditions and the like, a hand switch (emission switch) 8 for instructing a start of X-ray radiography (start of X-ray emission), a top board drive switch 9 for instructing driving of the top board 1, a top board drive controller 10 for performing drive control longitudinally of the top board 1 based on the instruction from this top board drive switch 9, an analog-to-digital converter 11 for digitizing and fetching X-ray detection signals from the FPD 3, and an image processor 12 for performing various processes (e.g. processes for creating X-ray fluoroscopic images) based on the X-ray detection signals outputted from the analog-to-digital converter 11.

The hand switch 8 instructs a start of X-ray emission when a button is depressed. The top board drive switch 9 includes a forward switch for advancing the top board 1 in one longitudinal direction thereof, and a backward switch for returning it in the opposite direction.

That is, a start of X-ray emission is instructed when the hand switch 8 is operated (e.g. the button is depressed) by the operator (e.g. an X-ray radiographer). The radiography controller 4 generates a high voltage in the emission controller 5 based on the X-raying conditions according to the sites to be imaged inputted from the input unit 6, for causing the X-ray tube 2 to emit X rays. The X-ray radiography is terminated when the hand switch 8 is released (i.e. the depression of the button is stopped). In a state of continuing operation of the hand switch 8 (continuing depression of the bottom), a sequential shooting is carried out to acquire a plurality of X-ray fluoroscopic images consecutively.

An automatic exposure detector 13 is disposed at outer edges on the X-ray incidence plane of the FPD 3 for detecting X rays emitted from the X-ray tube 2 and transmitted through the subject M.

The automatic exposure detector 13 is constructed, for example, of a fluorescent panel (not shown) which emits light corresponding to the intensity of X rays emitted from the X-ray tube 2 and transmitted through the subject M, and a photomultiplier tube (not shown) which converts the light emitted from this fluorescent panel into electric signals. That is, the automatic exposure detector 13 is constructed to output to the radiography controller 4 electric signals corresponding to an amount of X rays transmitted through the subject M.

Although the automatic exposure detector 13 is disposed at the outer edges on the X-ray incidence plane of the FPD 3 in Embodiment 1, it may be disposed only in predetermined locations (e.g. three locations) on the X-ray incidence plane of the FPD 3. A detector such as a photo pickup which detects incident X rays may be employed, or various detectors which can detect an amount of incident X rays may be employed.

The X-ray tube 2 noted above corresponds to the X-ray emitting device in this invention. The automatic exposure detector 13 noted above corresponds to the X-ray detecting device in this invention. The hand switch 8 noted above corresponds to the radiography start instruction input device in this invention. The top board drive switch 9 noted above corresponds to the drive instruction input device in this invention. The top board drive controller 10 noted above corresponds to the drive control device in this invention.

Next, the radiography controller 4, as shown in FIG. 1, includes a storage unit 14 for storing X-raying conditions indicating conditions of X-ray emission from the X-ray tube 2, an input detector 15 for detecting a start instruction from the hand switch 8 or a drive instruction from the top board drive switch 9 during a sequential shooting, an automatic exposure controller (AEC) 16 for carrying out automatic exposure control to maintain the luminance (density) of X-ray fluoroscopic images detected by the FPD 3 in a proper state through controls for starting, based on an input detection by the input detector 15, X-ray emission from the X-ray tube 2 on the X-raying conditions read from the storage unit 14, and for causing the emission controller 5 to stop the X-ray emission when the electric signals from the automatic exposure detector 13 reach a predetermined value (i.e. when the amount of transmitted X rays detected by the automatic exposure detector 13 reaches a predetermined value), and an X-raying condition fixing controller 17 for carrying out controls to cause an X-ray emission from the X-ray tube 2 on X-raying conditions effective when the X-ray emission is stopped by the automatic exposure controller 16, and turning off the automatic exposure control by the automatic exposure controller 16, until a next input is detected by the input detector 15.

The automatic exposure controller 16 has a timer 18 which, based on an input detection by the input detector 15 (detection of an X-ray emission start instruction from the hand switch 8 or detection of a top board drive instruction from the top board drive switch 9), measures an actual radiographing time from start of an X-ray emission from the X-ray tube 2 on the X-raying conditions read from the storage unit 14 until the amount of transmitted X rays detected by the automatic exposure detector 13 reaches the predetermined value.

Objects to be imaged (sites to be imaged), in a broad classification, include the head, chest, abdomen and legs, for example. In subdivided terms, the legs include the thighs, calves, and tips of the feet, for example. A radiographing direction may be frontal or sideways, for example. The X-raying conditions include a tube voltage, a tube current (tube current time product) and an X-ray emission upper limit time for determining X rays emitted from the X-ray tube 2, for example. The X-raying conditions corresponding to an object to be imaged, in the case of the front of the lower abdomen, for example, may be a tube voltage, a tube current (tube current time product) and an X-ray emission upper limit time corresponding to the front of the lower abdomen. Further, the X-ray emission upper limit time is a maximum X-ray emitting time from start of an X-ray emission. 0

The automatic exposure controller 16, as shown in FIG. 2, includes an integrator 21, a comparator/detector 22 and a reference voltage memory 23. The integrator 21 carries out time integration of the electric signals outputted from the automatic exposure detector 13, and outputs a voltage signal indicating a total amount of transmitted X rays to the comparator/detector 22. The comparator/detector 22 compares the voltage signal outputted from the integrator 21 and a reference voltage stored in the reference voltage memory 23 and indicating a predetermined amount of transmitted X rays corresponding to an object to be imaged (site to be imaged), and outputs an X-ray emission ending signal to the emission controller 5 when the two voltage values are in agreement, that is when the voltage signal outputted from the integrator 21 reaches the reference voltage. The reference voltages stored in the reference voltage memory 23 and corresponding to the objects to be imaged are inputted and set beforehand by the input unit 6.

The storage unit 14 noted above corresponds to the storage device in this invention. The input detector 15 noted above corresponds to the input detecting device in this invention. The automatic exposure controller 16 noted above corresponds to the automatic exposure control device in this invention. The X-raying condition fixing controller 17 noted above corresponds to the X-raying condition fixing control device in this invention. The timer 18 noted above corresponds to the actual exposure time measuring device in this invention.

The radiography controller 4 is constructed, upon receipt of a site to be imaged and a radiographing direction from the input unit 6, to read the X-raying conditions corresponding thereto from the storage unit 14, and output X-raying condition signals indicating the X-raying conditions (tube voltage, tube current and X-ray emission upper limit time) to the emission controller 5. Further, as shown in FIG. 3, the display unit 7 is constructed to display these site to be imaged, radiographing direction and X-raying conditions.

The radiography controller 4, upon receipt of an X-ray radiography start instruction (an X-ray emission starting signal indicating that an instruction for starting X-ray radiography has been given) from the hand switch 8, carries out a control for starting X-ray emission by outputting an X-ray emission starting signal to the emission controller 5.

The radiography controller 4 has a CPU (not shown) for performing various arithmetic control processes. Programs and data to be executed by this CPU (not shown) are stored beforehand in the storage unit 14. Various functions of this radiography controller 4 are realized by the CPU executing predetermined programs stored in the storage unit 14.

Next, as shown in FIG. 1, the emission controller 5 includes a tube voltage controller 24, a filament current controller 25 and a radiographing time controller 26. The tube voltage controller 24 converts a commercial supply voltage into a high voltage, and controls the voltage of the anode and cathode of the X-ray tube 2. The filament current controller 25 heats the filament (cathode) of the X-ray tube 2, and by controlling this, controls a current flowing to the X-ray tube 2. Specifically, the input of the X-raying condition signals outputted from the radiography controller 4 sets a voltage to be outputted from the tube voltage controller 24 and a current flowing to the X-ray tube 2 under control of the filament current controller 25. The radiographing time controller 26 controls the X-ray emission time of the X-ray tube 2 to be, at a maximum, up to the X-ray emission upper limit time at the time of automatic exposure control (when the automatic exposure control is on), and when the automatic exposure control is off, controls to stop the X-ray emission from the X-ray tube 2 at a time when the automatic exposure controller 16 stops the X-ray emission.

Figure 4:
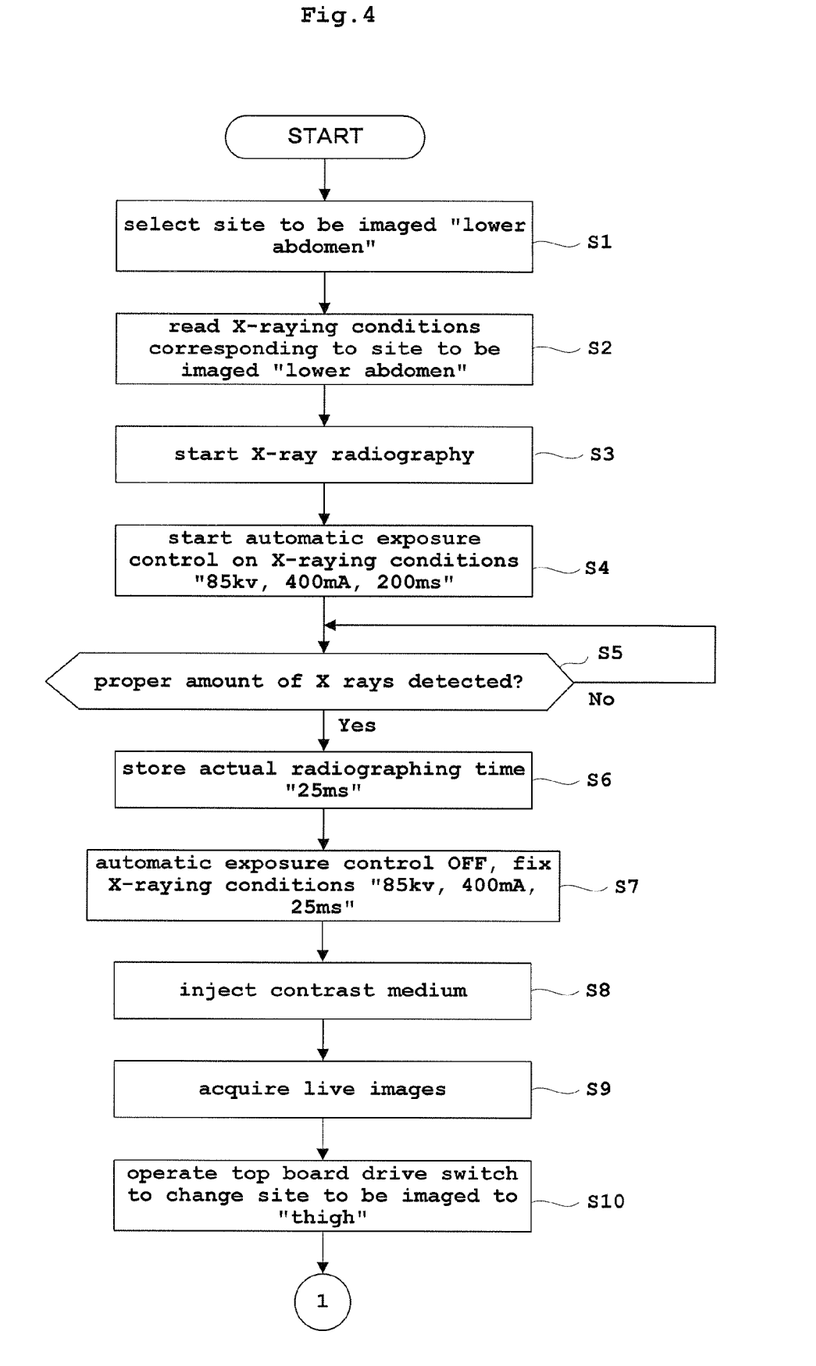
FIG. 4 is a flow chart showing a flow of operation in radiographing a procedure of pursuing blood flows from the lower abdomen to a leg with the X-ray apparatus in Embodiment 1.
Figure 5:
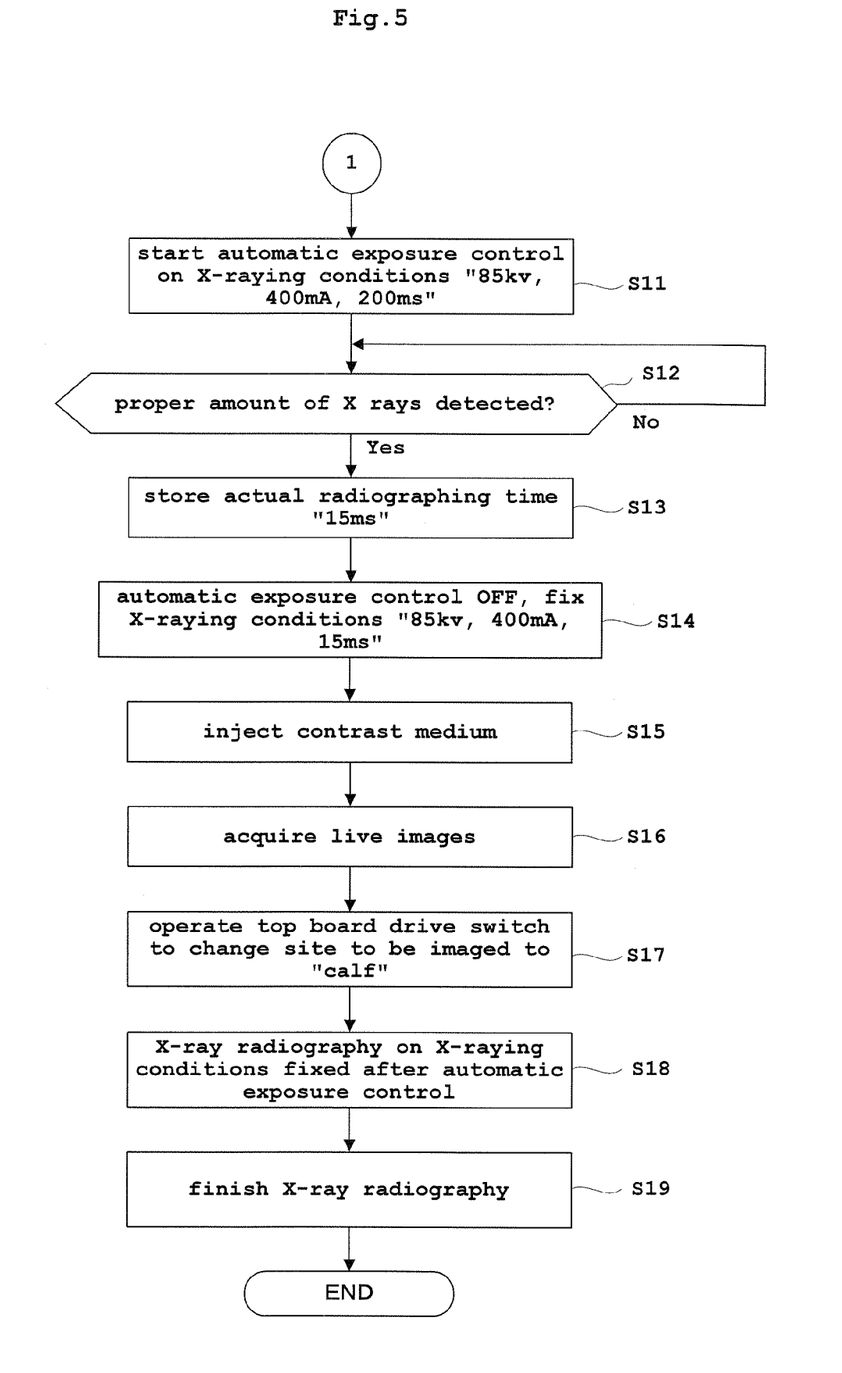
FIG. 5 is a flow chart showing the flow of operation in radiographing the procedure of pursuing blood flows from the lower abdomen to the leg with the X-ray apparatus in Embodiment 1.

Now, operation in radiographing a procedure, for example, of pursuing blood flows from the lower abdomen to a leg with this X-ray apparatus will be described in detail using also FIGS. 4 and 5. FIGS. 4 and 5 are flow charts showing a flow of operation in radiographing a procedure of pursuing blood flows from the lower abdomen to a leg with the X-ray apparatus in Embodiment 1

[Step S1] Select Site to Be Imaged

As shown in FIG. 4, the "lower abdomen" is selected as a site to be imaged. Specifically, the operator, using the input unit 6, selects and inputs the site to be imaged to be the "lower abdomen" on the display screen shown in FIG. 3. The operator selects also the radiographing direction to be "frontal", using the input unit 6.

[Step S2] Read X-Raying Conditions Corresponding to Site to Be Imaged "Lower Abdomen"

When the site to be imaged "lower abdomen" and the radiographing direction "frontal" have been selected in step S1, in step S2 the radiography controller 4 reads X-raying conditions "85 kv, 400 mA, 200 ms" corresponding to the above conditions from the storage unit 14, and outputs these values to the emission controller 5. These X-raying conditions are displayed on the display unit 7 as shown in FIG. 3. Here, 85 kv is a tube voltage value, 400 mA is a tube current value, and 200 ms is the X-ray emission upper limit time.

[Step S3] Start X-Ray Radiography

A top board driving operation by the operator drives the top board 1 to place the lower abdomen of the subject M between the X-ray tube 2 and FPD 3. When a proper position is attained, in step S3 the operator depresses the hand switch 8 to instruct a start of X-ray radiography. The emission controller 5 controls the X-ray tube 2 on these X-raying conditions "85 kv, 400 mA, 200 ms". That is, the tube voltage controller 24 controls the tube voltage of the X-ray tube 2 to "85 kv", the filament current controller 25 controls the tube current of the X-ray tube 2 to "400 mA", and the radiographing time controller 26 controls the X-ray emission time of the X-ray tube 2 for emission at the upper limit "200 ms".

[Step S4] Start Automatic Exposure Control

In step S4 the radiography controller 4 starts the automatic exposure control in response to the instruction for starting X-ray radiography given in step S3. That is, the automatic exposure control by the automatic exposure controller 16 is started simultaneously with start of X-ray emission, and the timer 18 of the automatic exposure controller 16 starts measuring an actual radiographing time.

[Step S5] Proper Amount of X Rays?

In step S5, the automatic exposure controller 16 determines, based on the electric signals from the automatic exposure detector 13, whether a proper amount of X rays has been reached, and controls to cut off the X-ray emission when the proper amount of X rays has been reached. Of course, a first X-ray fluoroscopic image (e.g. a mask image) has been acquired by the above cutoff time.

[Step S6] Store Actual Radiographing Time

In step S6, an actual radiographing time until the reaching time in step S5 is stored in the storage unit 14. Supposing, for example, the X-ray emission is cut off in "25 ms", since the timer 18 of the automatic exposure controller 16 clocks the X-ray emission time from start of the X-ray emission, the time taken until the time of X-ray emission cutoff ("25 ms" in this case) can be obtained. This "25 ms" is displayed on the display unit 7 as shown in FIG. 3.

[Step S7] Automatic Exposure Control OFF

In step S7, the radiography controller 4 turns off the automatic exposure control of the automatic exposure controller 16, and fixes the X-raying conditions to "85 kv, 400 mA, 25 ms". That is, until cancellation of the depression of the hand switch 8 or receipt of the operating instruction of the top board drive switch 9 described hereinafter, the radiography controller 4 controls X-ray radiography to be carried out for the second and subsequent images in the state of the automatic exposure control of the automatic exposure controller 16 turned off and the X-raying conditions fixed to "85 kv, 400 mA, 25 ms".

[Steps S8 and S9] Injection of Contrast Medium and Acquisition of Live Images

The subject M is injected with a contrast medium in step S8, and live images are acquired in step S9. That is, the operator continues depressing the hand switch 8, and a sequential shooting is being continued while the radiographic images of the subject M do not move from the lower abdomen (in short, until receipt of an instruction for driving the top board 1), in the state of the automatic exposure control turned off and the X-raying conditions fixed to "85 kv, 400 mA, 25 ms". Since the radiography can be continued on the same conditions even when the contrast medium flows in, radiographic images can be obtained in the same background density.

It should be noted that, in Embodiment 1, the hand switch 8 remains depressed, and a sequential shooting is carried out, except for a time when the top board drive switch 9 described hereinafter is being depressed.

[Step S10] Change Site to Be Imaged to "Thigh"

Assume, for example, that the operator, having finished acquiring live images of the lower abdomen in step S9 above, makes a change to the next site to be imaged "thigh". In step S10, the operator operates the top board drive switch 9 for driving the top board 1 longitudinally to place a thigh of the subject M between the X-ray tube 2 and FPD 3.

[Step S11] Start Automatic Exposure Control

After the top board driving operation by the operator is finished and the driving of the top board 1 is completed to place the thigh of the subject M between the X-ray tube 2 and FPD 3, in step S11 the emission controller 5 controls X-ray tube 2 on the X-raying conditions "85 kv, 400 mA, 200 ms". The radiography controller 4 starts the automatic exposure control in response to completion of this top board driving. That is, the automatic exposure control by the automatic exposure controller 16 is started after completion of this top board driving, and the timer 18 of the automatic exposure controller 16 starts measuring an actual radiographing time.

[Step S12] Proper Amount of X Rays?

In step S12, the automatic exposure controller 16 determines, based on the electric signals from the automatic exposure detector 13, whether a proper amount of X rays has been reached, and controls to cut off the X-ray emission when the proper amount of X rays has been reached. Of course, a first X-ray fluoroscopic image (e.g. a mask image) has been acquired from the resumption at the above cutoff time.

[Step S13] Store Actual Radiographing Time

In step S13, an actual radiographing time until the reaching time in step S12 is stored in the storage unit 14. Supposing, for example, the X-ray emission is cut off in "15 ms", since the timer 18 of the automatic exposure controller 16 clocks the X-ray emission time from start of the X-ray emission, the time taken until the time of X-ray emission cutoff ("15 ms" in this case) can be obtained. This "15 ms" is displayed on the display unit 7.

[Step S14] Automatic Exposure Control OFF

In step S14, the radiography controller 4 turns off the automatic exposure control of the automatic exposure controller 16, and fixes the X-raying conditions to "85 kv, 400 mA, 15 ms". That is, until cancellation of the depression of the hand switch 8 or receipt of the operating instruction of the top board drive switch 9, the radiography controller 4 controls X-ray radiography to be carried out for the second and subsequent images in the state of the automatic exposure control of the automatic exposure controller 16 turned off and the X-raying conditions fixed to "85 kv, 400 mA, 15 ms".

[Steps S15 and S16] Injection of Contrast Medium and Acquisition of Live Images

The subject M is injected with the contrast medium in step S15, and live images are acquired in step S16. That is, the operator continues depressing the hand switch 8, and a sequential shooting is being continued while the radiographic images of the subject M do not move from the lower abdomen (in short, until receipt of an instruction for driving the top board 1), in the state of the automatic exposure control turned off and the X-raying conditions fixed to "85 kv, 400 mA, 15 ms". Since the radiography can be continued on the same conditions even when the contrast medium flows in, radiographic images can be obtained in the same background density.

[Step S17] Change Site to Be Imaged to "Calf"

Assume, for example, that the operator, having finished acquiring live images of the "thigh" in step S16 above, makes a change to the next site to be imaged "calf". In step S17, the operator operates the top board drive switch 9 for driving the top board 1 longitudinally to place a calf of the subject M between the X-ray tube 2 and FPD 3.

[Step S18] X-Ray Radiography with Automatic Exposure Control and X-Raying Conditions Fixed In step S18, as in steps S11-S16, X-ray radiography is carried out with the automatic exposure control and X-raying conditions fixed for the site to be imaged "calf".

[Step S19] Finish X-Ray Radiography

In step S19, the X-ray radiography is finished since the series of X-ray photographing steps has been completed for the lower abdomen, thigh and calf of the subject M.

As described above, the X-ray apparatus in Embodiment 1 includes the top board 1 for supporting a subject M, the X-ray tube 2 for emitting X rays toward the subject M on the top board 1, the automatic exposure detector 13 opposed to the X-ray tube 2 across the top board 1 for detecting X rays emitted from the X-ray tube 2 and transmitted through the subject M, the storage unit 14 for storing X-raying conditions indicating conditions of X-ray emission from the X-ray tube 2, the hand switch 8 for receiving X-ray radiography start inputs, the top board drive switch 9 for receiving instruction inputs for driving the top board 1, the drive controller for performing drive control of the top board 1 based on an instruction from this top board drive switch 9, the input detector 15 for detecting a start instruction from the hand switch 8 or a drive instruction from the top board drive switch 9 during a sequential shooting, the automatic exposure controller 16 for starting, based on an input detection by the input detector 15, X-ray emission from the X-ray tube 2 on X-raying conditions read from the storage unit 14, and for stopping the X-ray emission from the X-ray tube 2 when an amount of transmitted X rays detected by the automatic exposure detector 13 reaches a predetermined value, and the X-raying condition fixing controller 17 for carrying out controls to cause an X-ray emission from the X-ray tube 2 on X-raying conditions effective when the X-ray emission is stopped by the automatic exposure controller 16, and turning off the automatic exposure control by the automatic exposure controller 16, until a next input is detected by the input detector 15. Thus, the automatic exposure control can be carried out only at the time of starting radiography, and a subsequent sequential shooting can be carried out in the state of X-raying conditions at that time being locked and the automatic exposure control being turned off. Supposing an attempt is made to carry out X-ray radiography of a new site to be imaged in place of a current site to be imaged, since a drive instruction from the top board drive switch 9 (i.e. instruction to drive the top board 1) is detected during the sequential shooting, the automatic exposure control can be carried out only at the time of starting radiography for the new site to be imaged by this drive instruction, and a subsequent sequential shooting can be carried out in the state of being locked to the X-raying conditions effective at that time, with the automatic exposure control turned off. As a result, a proper automatic exposure control can be carried out without setting a radiographic acquisition mode such as a subtraction mode, a mode of moving a radiographic system or a fluoroscopic table, or a non-moving mode.

At a time of sequential shooting for acquiring subtraction images, for example, there is no need for setting a subtraction mode, and a subsequent sequential shooting can be carried out in a state of being locked to X-raying conditions acquired from the automatic exposure control used only at the time of staring radiography, and with the automatic exposure control turned off. This allows a mask image and live images to be obtained on the same X-raying conditions, thereby to obtain proper subtraction images (difference images). Also in the case of an X-ray apparatus combined with a digital processing device without a function of notifying setting of the above mode, proper subtraction images (difference images) can be obtained similarly. When X-ray radiography is carried out for a plurality of sites as in leg DSA (digital subtraction angiography), the automatic exposure control is carried out once at the time of first radiography for the first site to be imaged, the X-raying conditions at that time can be locked, and X-ray radiography can be carried out on the locked X-raying conditions until a change is made in the sites to be imaged. When a shift is made to a different site to be imaged, by moving the radiographic system or the fluoroscopic table, the automatic exposure control is carried out once at the time of first radiography for the different site to be imaged, and the X-raying conditions at that time can be locked for X-ray radiography. Thus, proper subtraction images (difference images) can be obtained also when X-ray radiography is carried out for a plurality of sites.

Also when a sequential shooting is carried out to acquire live images without moving the radiographic system and top board 1 (fluoroscopic table), there is no need for setting the conventional "non-moving mode" or the like, and a subsequent sequential shooting can be carried out in a state of being locked to X-raying conditions acquired from the automatic exposure control used only at the time of staring radiography, and with the automatic exposure control turned off. This realizes a uniform luminance for all frames of a series of live images, without being influenced by a contrast medium such as barium.

That is, proper automatic exposure control can be carried out without setting the radiographic acquisition mode.

X-raying conditions are never locked unconditionally. When X-ray radiography is carried out for a plurality of sites, the automatic exposure control function can be turned on only at the time of starting radiography for each site to be imaged, thereby to obtain proper radiographic images.

The X-raying conditions include a tube voltage value of the X-ray tube 2, a tube current value of the X-ray tube 2 and an X-ray emission time value of the X-ray tube 2. The automatic exposure controller 16 has the timer 18 for measuring an actual radiographing time after starting X-ray emission from the X-ray tube 2 on the X-raying conditions read from the storage unit 14, based on an input detection by the input detector 15, until the amount of transmitted X rays detected by the automatic exposure detector 13 reaches a predetermined value. The X-raying condition fixing controller 17, until a next input is detected by the input detector 15, fixes the actual radiographing time measured by the timer 18 as X-ray emission time on the X-raying conditions, and turns off the automatic exposure control by the automatic exposure controller 16. Thus, the automatic exposure control can be carried out only at the time of starting radiography, and a subsequent sequential shooting can be carried out in the state of X-raying conditions at that time (X-ray emission time of the X-ray tube 2 acquired by the automatic exposure control) being locked and the automatic exposure control being turned off. Supposing an attempt is made to carry out X-ray radiography of a new site to be imaged in place of a current site to be imaged, since a drive instruction from the drive instruction input device (i.e. instruction to drive at least one of the X-ray emitting device and X-ray detecting device, and the top board 1) is detected during the sequential shooting, the automatic exposure control can be carried out only at the time of starting radiography for the new site to be imaged by this drive instruction, and a subsequent sequential shooting can be carried out in the state of being locked to the X-raying conditions effective at that time (X-ray emission time of the X-ray tube 2 acquired from the automatic exposure control), with the automatic exposure control turned off. As a result, a proper automatic exposure control can be carried out without setting a radiographic acquisition mode such as a subtraction mode, a mode of moving a radiographic system or a fluoroscopic table, or a non-moving mode.

The storage unit 14 stores X-raying conditions indicating conditions of X-ray emission from the X-ray tube 2, for each site to be imaged. Thus, X-raying conditions can be stored for various sites to be imaged, and various sites to be imaged can be X-rayed conveniently.

This invention is not limited to the foregoing embodiment, but may be modified as follows.

(1) The foregoing embodiment has been described, exemplifying the radiographic system (X-ray tube 2 and FPD 3) being fixed and the top board 1 being drivable. The invention is applicable also where the top board 1 is fixed and the radiographic system (X-ray tube 2 and FPD 3) is drivable. This can be realized by the input detector 15 adapted to detect an operation input of a drive switch which instructs driving of the radiographic system.

(2) The foregoing embodiment has been described, exemplifying the top board 1 for supporting a subject M. The invention is applicable also where the top board is contactable by the subject M (e.g. against which the subject M leans in a standing position). In this case, the radiographic system (X-ray tube 2 and FPD 3) may be constructed movable relative to the top board in an upstanding state, longitudinally (in an upstanding direction) of the top board. This can be realized by the input detector 15 adapted to detect an operation input of a drive switch which instructs driving of the radiographic system.

(3) In the foregoing embodiment, the FPD 3 is employed for detecting X rays transmitted through the subject M. However, various detectors such as an I.I tube may be employed.

(4) The foregoing embodiment has been described, exemplifying the hand switch 8 acting as the radiography start instruction input device. A different type of hand switch may be employed, which instructs an X-ray radiography start preparation when a button portion of this hand switch is pushed in by one step, and starts X-ray radiography when pushed in further. Instead of being limited to hand switches, various controllers (input devices) may be employed. The top board drive switch 9 is not limited to the type in the embodiment, but various controllers (input devices) may be employed.

(5) In the foregoing embodiment, the time when the amount of transmitted X rays reaches a predetermined value in the automatic exposure control is fixed as subsequent X-ray emission time. Instead, the tube voltage and tube current may be monitored, and values thereof may be fixed as subsequent X-raying conditions.

INDUSTRIAL UTILITY

As described above, this invention is suitable for X-ray apparatus for medical and industrial uses.

What is claimed is:

1. An X-ray apparatus for X-raying a subject, comprising (A) a top board for supporting, or contactable by, the subject; (B) an X-ray emitting device for emitting X rays toward the subject on the top board; (C) an X-ray detecting device opposed to the X-ray emitting device across the top board for detecting X rays emitted from the X-ray emitting device and transmitted through the subject; (D) a storage device for storing X-raying conditions indicating conditions of X-ray emission from the X-ray emitting device; (E) a radiography start instruction input device for receiving X-ray radiography start inputs; (F) a drive instruction input device for receiving instruction inputs for driving at least one of the X-ray emitting device and the X-ray detecting device, and the top board; (G) a drive control device for performing drive control of at least one of the X-ray emitting device and the X-ray detecting device, and the top board, based on an instruction from the drive instruction input device; (H) an input detecting device for detecting a start instruction from the radiography start instruction input device or a drive instruction from the drive instruction input device during a sequential shooting; (I) an automatic exposure control device for starting, based on an input detection by the input detecting device, an X-ray emission from the X-ray emitting device on X-raying conditions read from the storage device, and for stopping the X-ray emission from the X-ray emitting device when an amount of transmitted X rays detected by the X-ray detecting device reaches a predetermined value; and (J) an X-raying condition fixing control device for carrying out controls to cause an X-ray emission from the X-ray emitting device on X-raying conditions effective when the X-ray emission is stopped by the automatic exposure control device, and turning off the automatic exposure control by the automatic exposure control device, until a next input is detected by the input detecting device.

2. The X-ray apparatus according to claim 1, wherein the X-ray emitting device is an X-ray tube; the X-raying conditions include a tube voltage value of the X-ray tube, a tube current value of the X-ray tube and an X-ray emission time value of the X-ray tube; the automatic exposure control device has an actual radiographing time measuring device for measuring an actual radiographing time after starting the X-ray emission from the X-ray emitting device on the X-raying conditions read from the storage device, based on an input detection by the input detecting device, until the amount of transmitted X rays detected by the X-ray detecting device reaches the predetermined value; and the X-raying condition fixing control device, until a next input is detected by the input detecting device, fixes the actual radiographing time measured by the actual radiographing time measuring device as X-ray emission time on the X-raying conditions, and turns off the automatic exposure control by the automatic exposure control device.

3. The X-ray apparatus according to claim 2, wherein the storage device stores X-raying conditions indicating conditions of X-ray emission from the X-ray emitting device, for each site to be imaged.

* * * * *